United States Patent [19]
Poulos et al.

[11] Patent Number: 5,279,314
[45] Date of Patent: Jan. 18, 1994

[54] ELECTRIC DENTAL FLOSSER

[75] Inventors: Louis Poulos, Mountain View; Leonard L. Hofheins; Del M. Thornock, both of Concord, all of Calif.

[73] Assignee: Advanced Dental Research Corporation, San Jose, Calif.

[21] Appl. No.: 812,725

[22] Filed: Dec. 23, 1991

[51] Int. Cl.$^5$ .............................................. A61C 15/00
[52] U.S. Cl. ..................... 132/322; 132/325
[58] Field of Search ............... 132/322, 323, 324, 325, 132/329

[56] References Cited

U.S. PATENT DOCUMENTS

| | | | |
|---|---|---|---|
| 3,421,524 | 1/1969 | Waters | 132/322 |
| 3,667,483 | 6/1972 | McCabe | |
| 3,759,272 | 9/1973 | Di Vincenti | |
| 3,759,273 | 9/1973 | Knaus | |
| 3,759,274 | 9/1973 | Warner | |
| 3,847,167 | 11/1974 | Brien | |
| 3,892,249 | 7/1975 | Jones et al. | 132/323 |
| 4,014,354 | 3/1977 | Garrett | 132/322 |
| 4,235,253 | 11/1980 | Moore | |
| 4,245,658 | 1/1981 | Lecouturier | |
| 4,265,257 | 5/1981 | Salyer | |
| 4,307,740 | 12/1981 | Florindez et al. | 132/322 |
| 4,326,549 | 4/1982 | Hinding | |
| 4,338,957 | 7/1982 | Meibauer | |
| 4,458,702 | 7/1984 | Grollimund | |
| 4,605,025 | 8/1986 | McSpadden | |
| 4,706,695 | 11/1987 | Urso | |
| 4,982,752 | 1/1991 | Rodriguez | 132/327 |
| 5,056,540 | 10/1991 | Page | 132/323 |

*Primary Examiner*—Gene Mancene
*Assistant Examiner*—Cindy A. Cherichetti
*Attorney, Agent, or Firm*—Janet K. Castaneda; James E. Eakin

[57] ABSTRACT

A light electric dental flosser with a rechargeable battery compartment includes a motor casing, interchangeably individualized head units, and disposable plastic floss tips that snap mount within the hinged end of the head unit. The floss tips exhibit bidirectional flossing motion provided from a motion translation system including an eccentric cam, a yoke, and an output shaft with a cam follower mechanism that follows a generally Z-shaped tracking surface with a vertical track component and a horizontal track component enabled by the yoke to complete the resulting "Z" movement. The floss tips have a molded-in filament and are molded from a shock absorbing substance which absorbs the vertical component of the "Z" shaped motion upon the application of pressure to the filament thereby outputting horizontal motion until the filament passes through the contact area between two teeth. In an automatic mode, an infrared sensor in the head activates the motor when the line of sight between infrared sensors is broken by the filament approaching a contact area between two teeth.

51 Claims, 10 Drawing Sheets

ELECTRIC DENTAL FLOSSER

FIELD OF THE INVENTION

The present invention relates to an electric dental flosser. More particularly, the invention relates to an electric dental flosser with disposable floss tips, individualized removable heads for multiple users, and multidirectional flossing motion.

BACKGROUND OF THE INVENTION

Satisfactory oral hygiene practices include the use of dental floss as an interdental cleaner. Approximately ninety percent (90%) of all dental disease originates between the teeth, an area ineffectually cleaned by existing manual and electric tooth brushes. Unchecked bacterial proliferation between the teeth may cause dental plaque and consequent gum disease. Gum disease is the leading cause of tooth loss.

Dental floss is currently the most widely prescribed interdental cleaning aid. For manual use, the individual typically maneuvers a length of dental floss back and forth across the contact point between two teeth until the floss passes through the contact point into the interproximal space between the teeth. The floss is then pressed against the tooth surface and moved vertically up and down against the surface to clean the tooth.

Proper use of dental floss is essential for thorough interdental cleaning. Proper manual flossing technique includes horizontal motion of the floss until the floss passes through the contact point, followed primarily by vertical movement of the floss to clean the tooth once the floss is in the interproximal area.

Frequently, users mistakenly apply downward pressure to force the floss through a tight contact point thereby causing the floss to snap against the gingiva causing damage thereto, such as "floss cuts". Gingiva damage from improperly flossing techniques may contribute to the formation of gum disease.

Most adults have silver or composite filling materials between the teeth which increase the difficulty in maneuvering the floss through tight contact points. Dental fillings frequently include sharp or irregular edges which may cause the floss to shred, break or become stuck in the contact area. Users may also fail to vertically manipulate the floss against the tooth in a manner calculated to clean the entire tooth surface.

The principle reported problem with dental floss is the publics' reluctance to floss on a regular basis, or to floss at all. Individuals are reluctant to place their fingers in the mouth. Studies have also shown that individuals report dental floss is difficult to handle, and that flossing is extremely unpleasant, hard to perform, and time consuming.

Dental floss holders and threaders are available to eliminate the necessity of placing the fingers in the mouth while flossing. Such floss holders do not solve the problem of incomplete and improper manual flossing techniques.

Power driven dental flossing devices are described in prior art literature, but tangible prototypes and/or commercial embodiments of such devices are not believed to exist. A number of these described devices merely reciprocate floss between the teeth. Such devices are described in U.S. Pat. No. 3,759,274 and U.S. Pat. No. 4,014,354.

Several prior art power driven dental flossing devices combine reciprocation of floss and vertical oscillation. One such device is described in U.S. Pat. No. 4,706,695. The user is required to manually work the floss through the contact point prior to powered advancement of floss through a vertically oscillating, tined tip to a take-up spool for used floss. U.S. Pat. No. 4,338,957 incompletely describes a flosser with reciprocating floss and vertical oscillation. The device in U.S. Pat. No. 4,307,740 is similar to the '957 device and includes vertical oscillation with simultaneous reciprocation of floss.

Another prior art flosser is found in U.S. Pat. No. 4,605,025 which describes circular or ovoid floss oscillation produced by vertical motion from an oscillating unit. U.S. Pat. No. 4,235,253 describes a flosser where the floss must be worked manually through the teeth prior to vertical oscillation. U.S. Pat. No. 4,245,658 describes horizontal movement applied to the headpiece which holds the tines.

Other prior art power driven flossing devices are designed to attach to power tooth brushes, such as the device shown in U.S. Pat. No. 4,830,032.

None of the above described prior art flossers provide automatic, powered, high torque horizontal motion through the tight contact points with a vertical motion component added in the interproximal space. Additionally, most of the described devices use spools of dental floss which undesirably store bacteria contaminated, used floss within the device, and which require the user to periodically perform floss replacement and difficult manual re-threading operations.

As may be seen by the above discussion of the prior art, a heretofore unmet need exists for a power driven dental flosser that is easy to use, safe, provides high torque horizontal motion to pass the floss through the tight contact points without snapping the floss against the gums, and then provides a combined vertical/horizontal pattern of motion while the floss is in the interproximal area to effectively remove bacterial plaque in this critical area.

SUMMARY OF THE INVENTION WITH OBJECTS

A general object of the present invention is to provide an electric dental flosser that is easy to use, safe, and overcomes the limitations and drawbacks of the prior art.

A specific object of the present invention is to provide an electric dental flosser that enables effective and rapid flossing of the teeth and includes a floss tip that moves horizontally until the floss passes through the entrance to or exit from the contact points, and moves in a combined vertical/horizontal pattern of motion while the floss is in the interproximal area.

Another specific object of the present invention is to provide an electric dental flosser with disposable floss tips for sanitation purposes and for ease of use.

Yet another specific object of the present invention is to provide an electric dental flosser with individualized detachable head units for multiple users.

Still another specific object of the present invention is to provide an electric dental flosser having the disposable tip component constructed from shock-absorbing materials, the disposable tip including a molded in floss filament thereby eliminating the need for manual re-threading procedures.

Yet one more specific object of the present invention is to provide an electric dental flosser having an automatic pressure activation mode.

Still one more specific object of the present invention is to provide a lighted electric dental flosser with an auxiliary battery power source.

A further specific object of the present invention is to provide an electric dental flosser that provides horizontal motion of the floss tip until the floss has passed through the tight contact area, and then provides a combined horizontal/vertical "Z" shaped motion of the floss tip within the interproximal space, said "Z" shaped motion eliminating the need for manual dexterity to properly floss the teeth.

In accordance with the present invention, an electric dental flosser is powered by an electric motor energized by a rechargeable battery power source. A conventional planatary reduction gearbox reduces the speed of the motor to achieve the desired flossing motion. Alternatively, a potentiometer may be provided to reduce the speed of the motor. A three-way switch, or magnetic Hall effect switch, is connected to the battery and operated by a slide button provided with automatic mode, manual mode and off positions. The motor and battery components are sealed from the remaining components in an elongated power casing. A recharging unit is provided.

Individualized removable head units attach to the power casing for multiple users. The head units are color-coded for user identification. The lighted head units are formed from mating housing sections and each defines prongs at a U-shaped end thereof. A hinge mechanism in the U-shaped end of the mating housing sections enables the end of the housing to open for insertion and removal of a disposable floss tip. A contact sensor is mounted in the U-shaped end within the cavity formed by the mating housing sections.

The multi-directional movement of the electric flosser is provided by a motion translation system attached at one end to the motor, and at the opposite end to the disposable floss tip. The motion translation system is secured within the cavity formed by the mating housing sections by seating slots defined therein. The motion translation system includes a motor linkage, an eccentric cam attached to the motor linkage, a yoke attached to the eccentric cam, and an output shaft attached to the yoke. The eccentric cam provides horizontal movement of the yoke. The shaft/yoke interface includes cam follower points which follow a generally "Z" shaped tracking surface defined in the head housing. The Z-shaped tracking surface includes a vertical track component and a horizontal track component enabled by the yoke to complete the resulting "Z" movement of the output shaft.

The floss tips snap onto the anterior end of the output shaft which extends into the U-shaped end of the removable head unit. The floss tips are disposable units molded from a shock absorbing substance and including a molded in floss filament spanning tines formed at the end of each U-shaped floss tip. A plurality of grooves are defined in the tines. When the floss tip is snapped onto the output shaft and the U-shaped end of the head unit is closed, the floss filament is outside of the head unit and the tines are inside the head unit in the cavity thereof.

When operating the dental flosser in the automatic mode, the user inserts the head unit into the mouth and the contact sensor in the U-shaped prongs of the head sends a signal to the switch for the battery to activate the motor when the line of sight between infrared sensors in the prongs is broken by the floss filament approaching a contact area between two teeth. The contact sensor may also be a fiber optics device or a stress sensor where the motor is activated when the floss filament touches the teeth. The tension on the floss filament as it presses on the contact area is transferred to the shock-absorbing floss tip and grooved tines which absorb the vertical component of the "Z" shaped motion from the output shaft thereby producing only horizontal motion until the floss filament has passed through the contact area to relieve the tension on the floss filament. "Z"-shaped motion of the floss tip occurs in the interproximal space throughout the flossing process.

The motor is energized by the switch at all times in manual mode. In another aspect of the present invention, the motor is energized and a mechanical clutch disengages the shaft until the floss contacts a tooth. Movement of the floss tip only occurs with contact between the floss and a tooth.

In another aspect of the present invention, the floss filament is replaceable.

These and other objects, aspects, advantages and features of the present invention will be more fully understood and appreciated upon consideration of the following detailed description of preferred embodiments, presented in conjunction with the accompanying drawings.

BRIEF DESCRIPTION OF THE DRAWINGS In the Drawings.

DESCRIPTION OF A PREFERRED EMBODIMENT

Figure 1A:
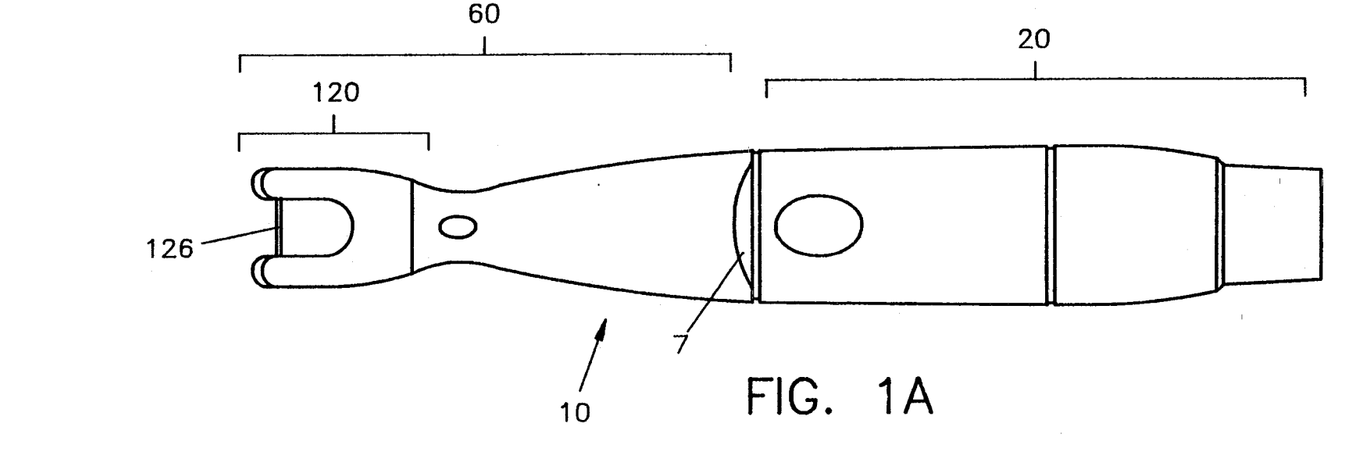
FIGS. 1A and 1B are, respectively, top and side views of a preferred embodiment of the assembled electric flosser of the present invention.
Figure 1B:
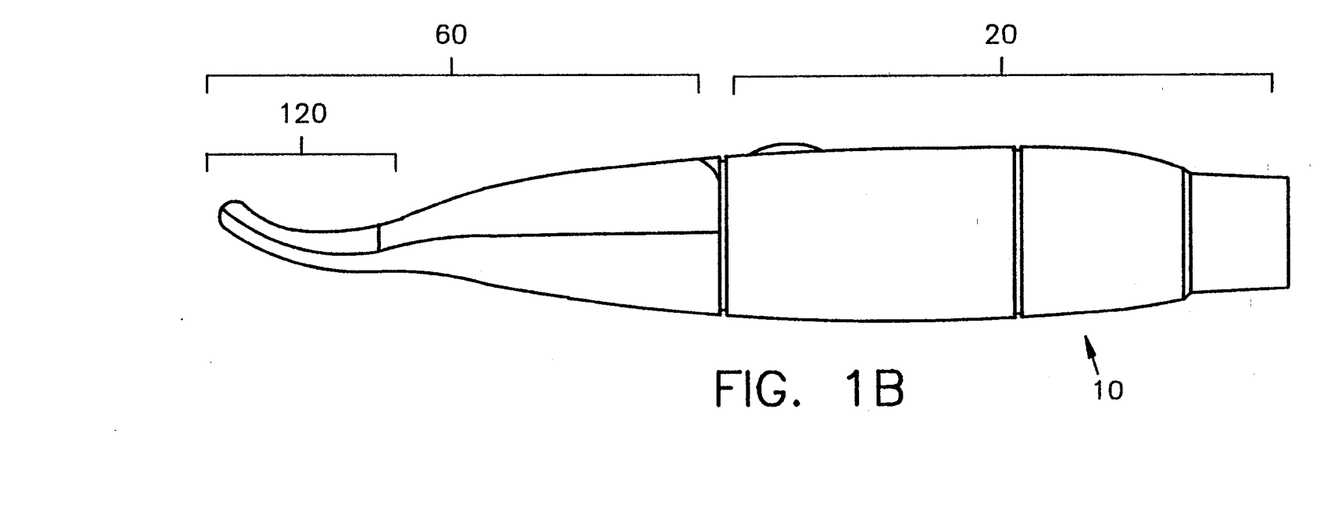

A preferred embodiment of the electric dental flosser of the present invention is shown generally as 10 in FIG. 1. The hand-held flosser 10 generally includes a power unit 20, a head unit 60, and a disposable floss tip 120.

Figure 1C:
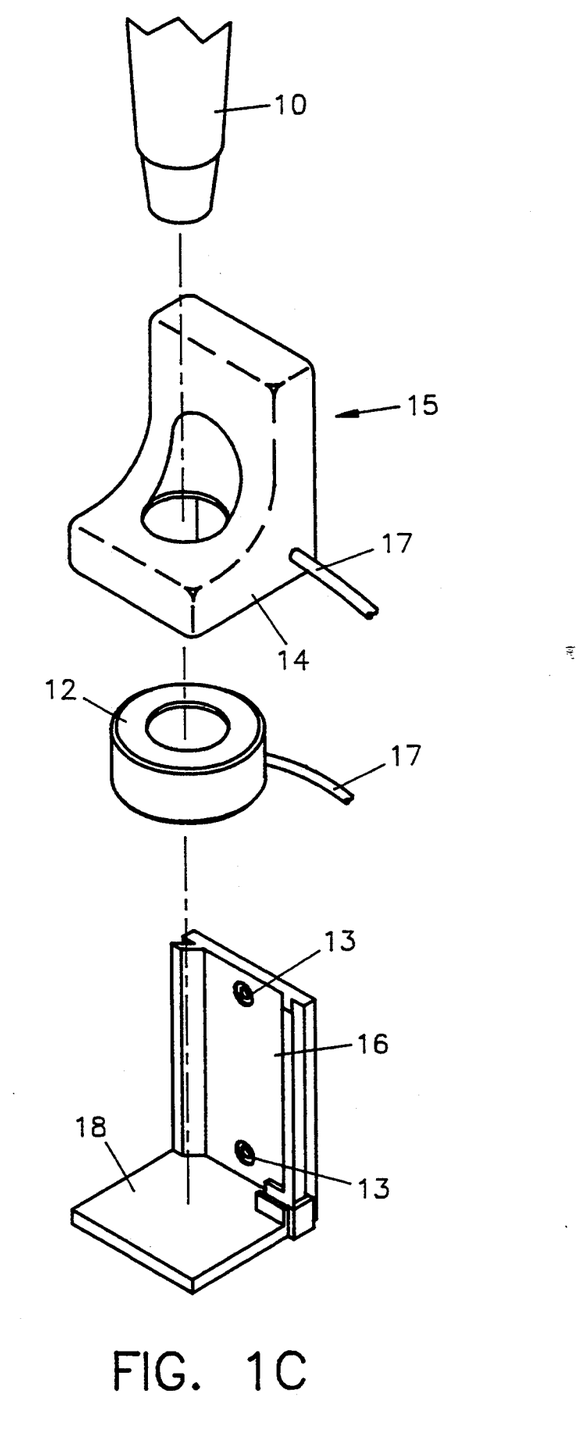
FIG. 1C is an elevated perspective and exploded view of a recharging unit shown with the electric flosser.

A recharging unit 15 is shown in exploded view in FIG. 1C. The unit 15 includes the recharging pod 12 and electrical cord 17, which mounts within the housing 14. The housing 14 includes two planar mounting walls 16, 18. Apertures 13 are provided so that the unit 15 may be mounted with screws on the wall or on a counter. Alternatively, the unit 15 may simply be placed upon a counter.

THE POWER UNIT 20

Referring to FIGS. 2-5, the components of the power unit 20 are housed in an elongated tubular casing 22 which is preferably molded or cast from a rigid plastic substance such as polycarbonate, ABS plastic, polyethylene, or polystyrene. The hand-held casing 22 includes a unitary charging coil casing section 24, a unitary tubular battery casing section 26, and a unitary tubular motor casing section 28.

Figure 2:
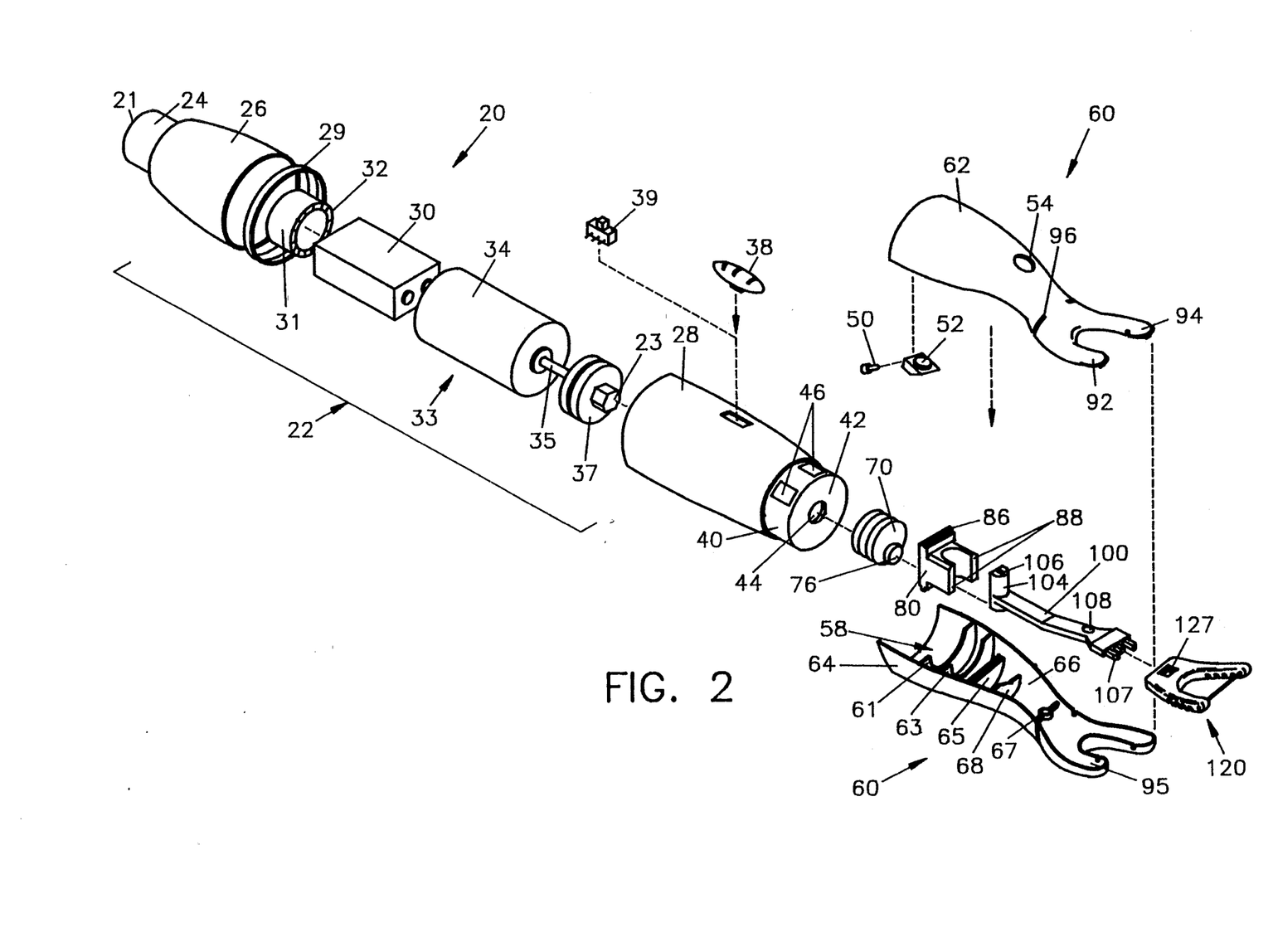
FIG. 2 is an elevated perspective view of the unassembled components of the electric flosser of FIG. 1 with an exploded view of the head.
Figure 3:
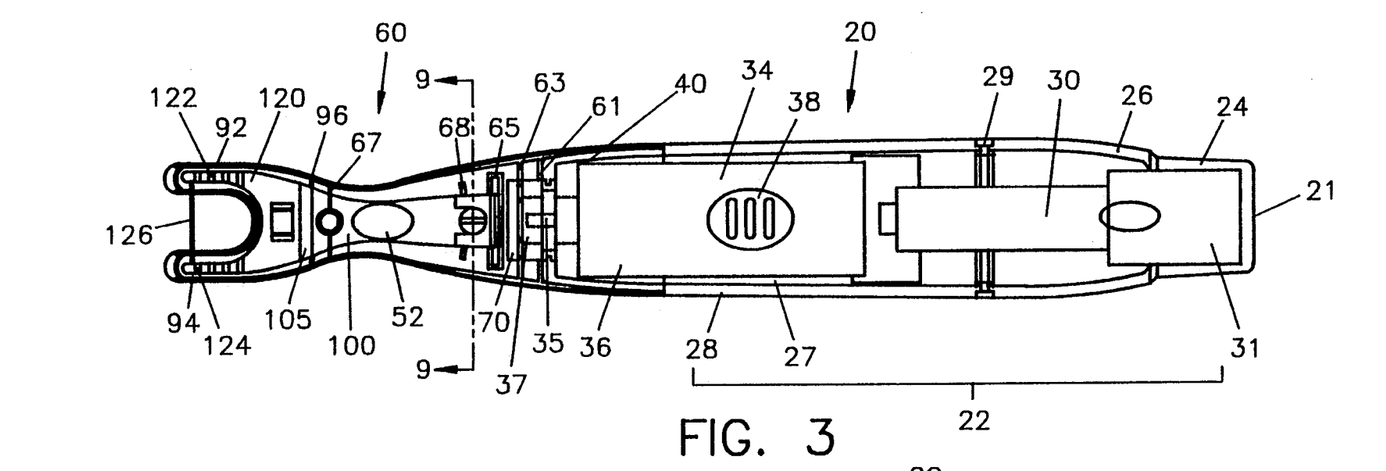
FIG. 3 is a top plan view of the electric flosser of FIG. 1 showing the arrangement of the components within the assembled casing and housing.
Figure 4:
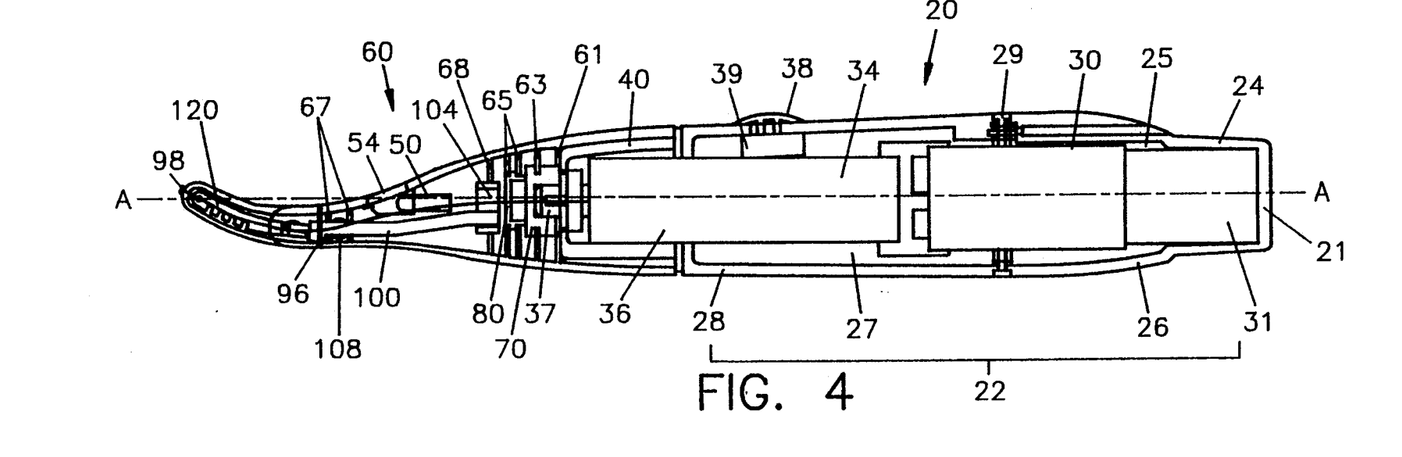
FIG. 4 is a side plan view of the electric flosser of FIG. 3.

The tubular charging coil casing 24 defines a circular end wall 21 and an interior space 25 housing an induction, non-contact recharging coil unit 31.

The tubular battery casing section 26 houses a preferred 1.2 Volt rechargeable NiCad battery 30. A pressure plate 32 is provided to maintain electrical contact between the battery 30 and the motor 34.

A gasket 29 made from a flexible material, preferably a synthetic rubber material, provides a water-tight seal between the open ends of the battery section 26 and the motor section 28. In the preferred embodiment, the battery section 26 and the motor section 28 are permanently sealed together to form one unitary piece.

The motor casing section 28 defines an interior tubular space 27 containing a motor housing 33. The motor housing 33 contains a conventional low voltage D.C. electric motor 34, such as an Autotrol (tm) 6 volt motor with a conventional reduction gearbox 36, such as an Autotrol (tm) 45 to 1 gear reduction device, attached to the motor 34. The reduction gearbox 36 reduces the speed of the motor 34 to approximately 900 RPMs. A motor shaft 35 extends axially from the motor housing 33. A motor linkage interface 37 engages the motor shaft 35 for rotation therewith.

The motor casing 28 defines at its anterior end a collar portion 40 including a circular end wall 42 and aperture 44. Internal gaskets (not shown) surround the aperture 44 to prevent moisture from entering the motor-battery-coil compartment. Two electrical contacts 46 are embedded in the collar 40. The contacts 46 are wired (not shown) to the switch 39. The motor linkage interface 37 extends axially through the aperture 44.

A sliding thumb button 38 mounted through the motor casing section 28 operates a three-position conventional switch 39 to provide the user with off, automatic and manual operating switch positions. The switch 39 may also be a magnetic Hall effect sensor switch or the like thereby eliminating the need for the switch opening into the motor compartment. In the shown switch aspect, internal gaskets (not shown) are provided on the thumb button to prevent moisture from entering the compartment. The generally elliptical button 38 is preferably constructed from ABS plastic. The switch 39 is wired to the battery 30 (not shown). The off switch position disconnects power from the battery 30 to the motor 34. The automatic and manual modes of operation will be described later in connection with the description of the use of the flosser 10.

THE HEAD UNIT 60

Referring now to FIGS. 2-4, 10 and 15, the elongated head unit 60 is preferably molded from a rigid plastic such as polypropylene and includes top section 62 and mating bottom section 64. Color-coded dots 7 (FIG. 1) are provided on the head unit for identification purposes. A high intensity, vacuum sealed low voltage lamp 50, such as a GTE Sylvania miniature halogen 6 volt lamp, is housed in a molded focusing polycarbonate lens mechanism 52 which is installed in an ovoid opening 54 in top section 62. The low voltage lamp 50 is wired to an electrical contact 56 embedded within the plastic of the top section 62. The electrical contact 56 interfaces with the electrical contact 46 in the collar 40 of the motor casing 28. Sections 62 and 64 each define axial cavities 66 including mating, transverse seating slots 61, 63, 65, and 67.

Figure 10:
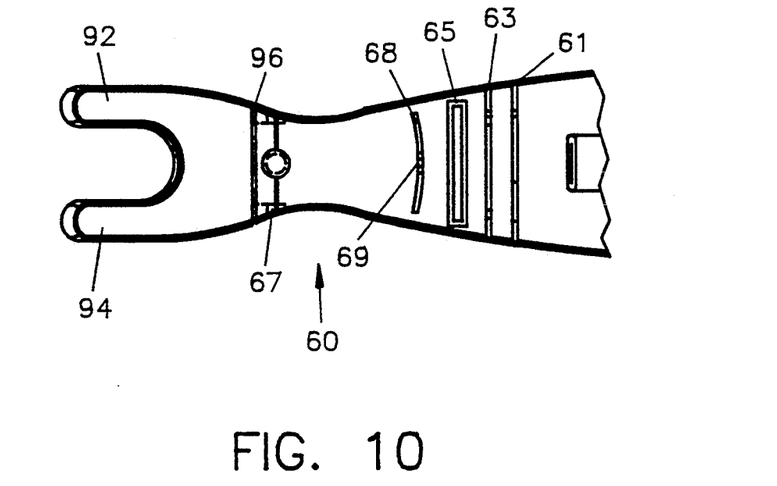
FIG. 10 is a top plan view of a head housing section showing the motion translation mounting slots and the hinge.
Figure 11:
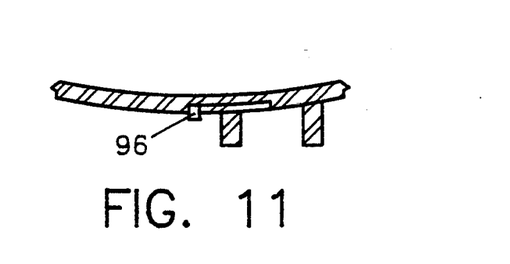
FIG. 11 is a side sectional view of the hinge in the head housing.

Seating slots 61 and 63 define in both top and bottom cavities 66 paired transverse walls with semi-circular openings 58 for securing a cam 70 within the head unit 60. When the top and bottom sections 62,64 are assembled, the seating slots 61 and 63 form a circular collar and four side walls for securing the position of the cam 70.

Figure 7A:
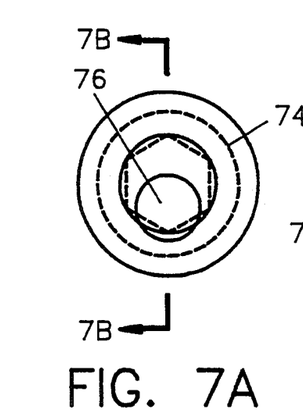
FIG. 7A is a front end view of the eccentric cam.
Figure 7B:
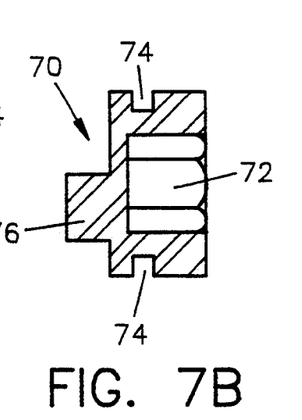
FIG. 7B is a side sectional view taken along the lines 7—7 in FIG. 7A.
Figure 7C:
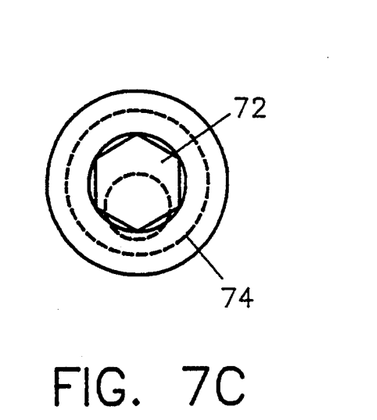
FIG. 7C is a rear end view of the eccentric cam.
Figure 8A:
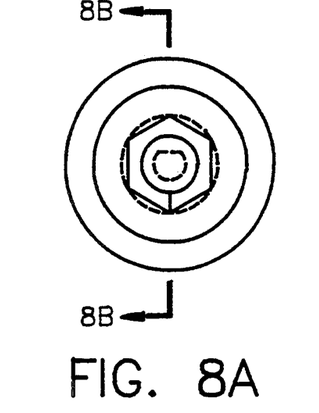
FIG. 8A is a front end view of the motor linkage.
Figure 8B:
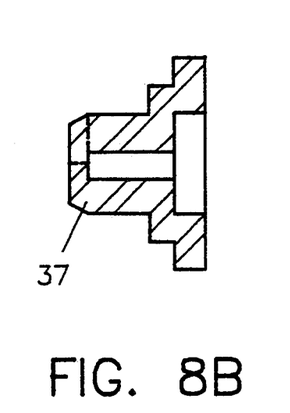
FIG. 8B is a side sectional view of the linkage taken along the lines 8—8 in FIG. 8C.
Figure 8C:
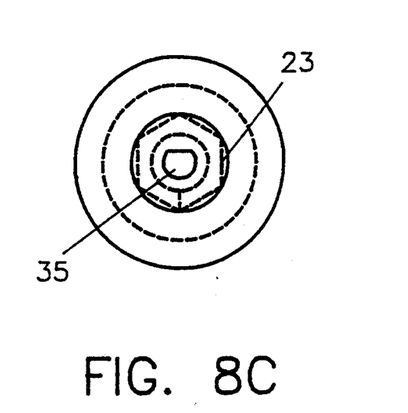
FIG. 8C is a rear end view of the linkage.
Figure 9A:
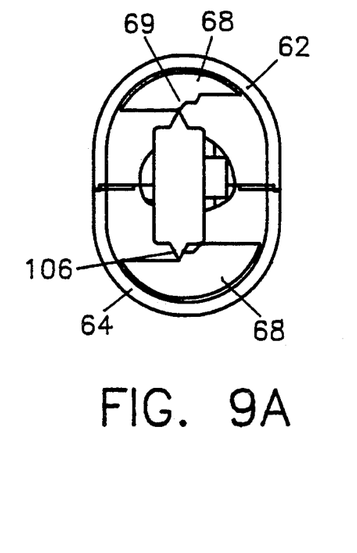
FIGS. 9A, 9B and 9C are plan sectional views taken along the lines 9—9 in FIG. 3 and showing the cam follower point on the output shaft following the Z-shaped cam structure in the head housing.
Figure 9B:
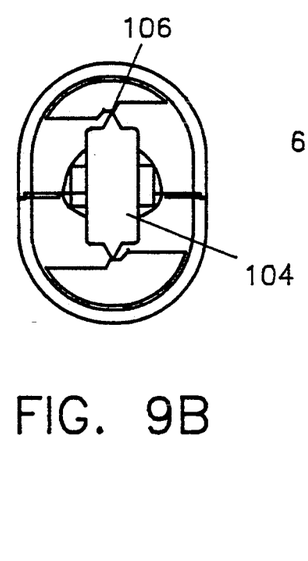
Figure 9C:
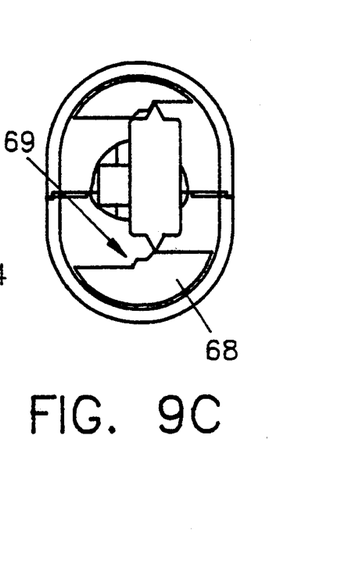

The generally cylindrical cam body 70 is preferably molded from a plastic such as Delrin (tm). As best shown in FIGS. 7A-7C, the cam 70 defines a hexagonal opening 72 for receipt of a mating axial, hexagonal extension 23 on the linkage interface 37, which is also preferably molded from Delrin (tm). A channel 74 is defined around the circular cam body 70 for mounting the cam 70 in the collar formed by the seating slots 61,63. A generally circular peg 76 extends axially from the anterior end of the cam 70 and is offset preferably 3 mm, ±0.5 mm, from the center of the cam body 70.

Figures 6A, 6B:
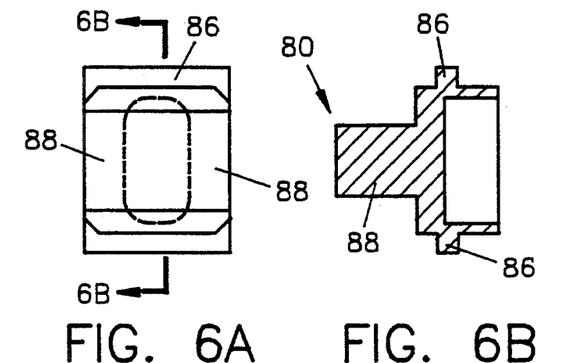
FIG. 6A is a front end view of the yoke.
FIG. 6B is a side sectional view of the yoke.
Figure 6C:
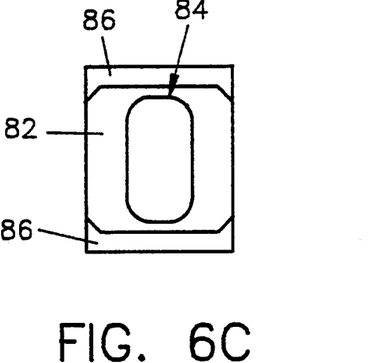
FIG. 6C is a rear end view of the yoke.

The seating slots 65 transversely arrayed in the top and bottom sections 62, 64 define a generally rectangular slotted enclosure for mounting a yoke 80 within the head 60. The yoke 80 is preferably molded from polycarbonate. As best shown in FIGS. 6A-6C, the yoke 80 defines a back wall 82 having an ovoid slot interface 84 for engaging the peg 76 of the cam 70. The back wall 82 further defines top and bottom rims 86 for sliding engagement within the rectangular enclosure formed by the seating slots 65. The transverse length of the slotted enclosure is longer than the yoke 80 by approximately 3 mm, ±0.5 mm, thereby enabling the rims 86 of the yoke 80 to slide back and forth linearly in the slotted enclosure transverse to the axis of the head 60. Paired axially extending arms 88 form a generally U-shaped enclosure.

The output shaft 100 is mounted within the U-shaped enclosure formed by the arms 88. The output shaft 100 is preferably molded from polycarbonate and includes a posterior mounting portion 102, a shank portion 103, and anterior portion 105.

Figure 5A:
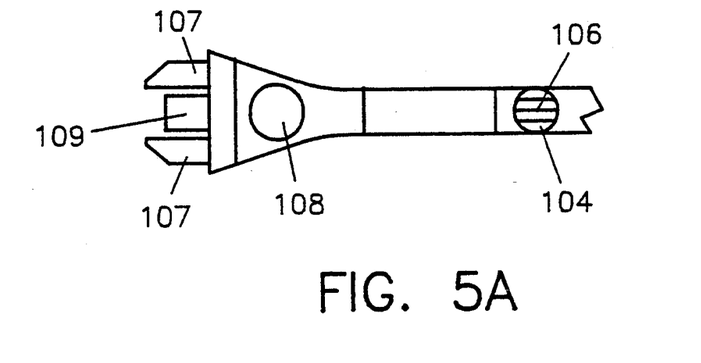
FIG. 5A is a top plan view of the output shaft.
Figure 5B:
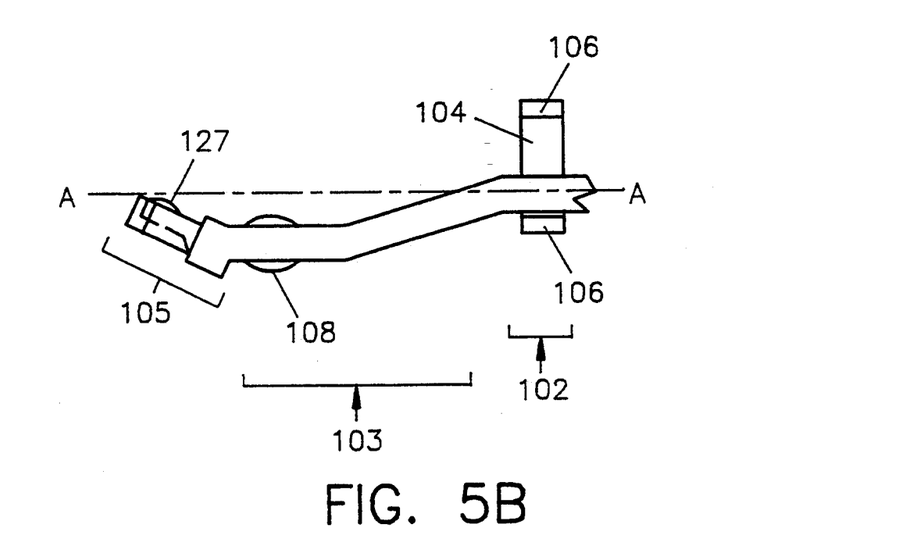
FIG. 5B is a side plan view of the output shaft.
Figure 5C:
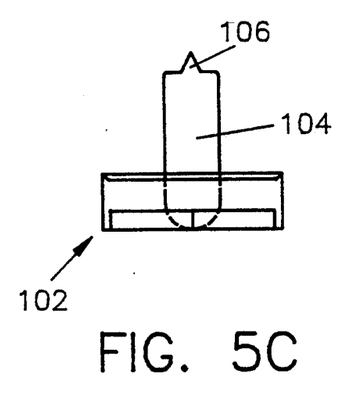
FIG. 5C is a rear plan view of the output shaft showing the cam follower mechanism.
Figure 5D:
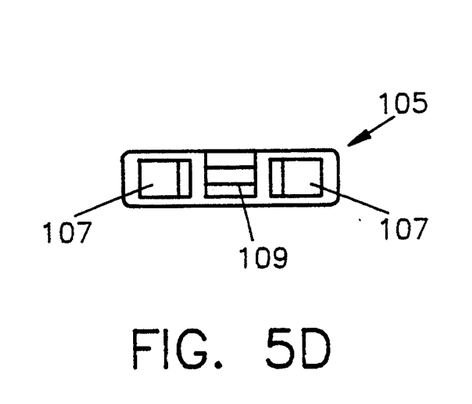
FIG. 5D is a front plan view of the output shaft showing the snap mounting mechanism for the floss tip.

As best seen in FIG. 5B, the shank portion 103 of the output shaft 100 gradually extends from the midline "A" of the axis of the flosser 10 to an axially extending, but offset, portion which defines a generally circular pivot mount 108 for engagement within a circular socket formed by the mating seating slots 67 in top and bottom head sections 62, 64. The circular pivot mount 108 enables the shaft 100 to pivot and swivel within the circular socket for horizontal and vertical movement of the shaft 100.

As best seen in FIGS. 5A–5D and 9A–9C, the axially aligned posterior portion 102 of the shaft 100 defines a body portion 104 for engagement within the U-shaped enclosure formed by the arms 88. The output shaft 100 is thereby secured within the head 60 in the yoke 80 and in the seating slots 67. The body portion 104 further defines top and bottom axially aligned cam follower edges 106 for engagement with a tracking surface 69.

Referring now to FIGS. 2, 9A–9C, and 10, a transverse wall 68 extends perpendicularly to the axis of and within both the top and bottom sections 62,64. The walls 68 each define a tracking surface 69 that describes a generally "Z"-shaped path having a 3 mm horizontal component and a 2 mm vertical component relative to the axis of the flosser 10. As a result of the cam follower edges 106 following the path of the tracking surface 69, the output shaft 100 moves in a generally "Z"-shaped path in a manner to be further described.

The anterior portion 105 of the output shaft 100 gradually extends towards the midline "A" of the axis of the flosser 10 and defines a snap-mounting mechanism including a pair of snap mounting fingers 107 and a snap release tab 109.

Referring now to FIGS. 2–4, 10, 11 and 12, the anterior portion 105 of the output shaft 100 extends into the apex 90 of the head 60. The apex 90 is generally U-shaped and defines two prongs 92, 94 which extend across the midline "A" of the axis of the flosser 10. A living hinge 96 is preferably molded from polypropylene and defined transversely in the apex 90 to enable the top and bottom sections 91,93 of the apex 90 to open upon depression of a pair of tabs 98.

Figure 12:
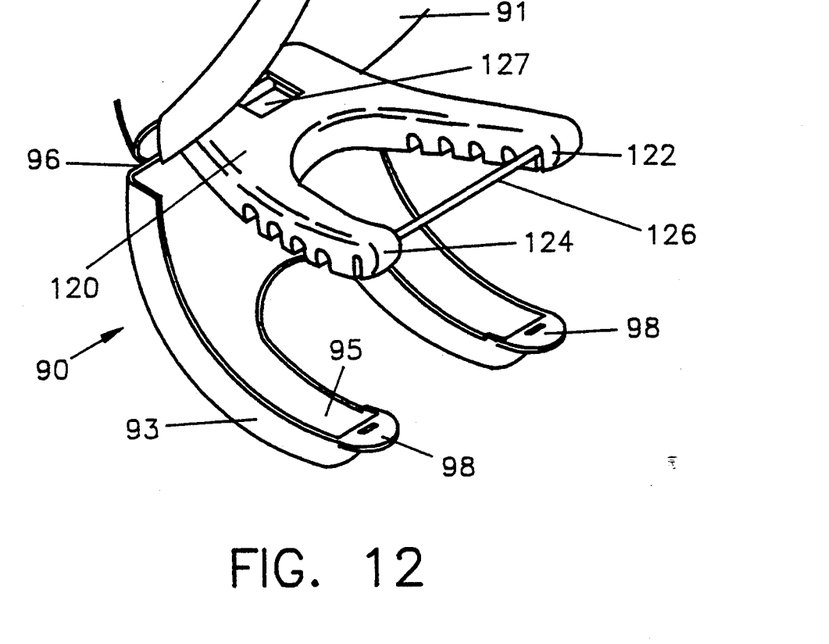
FIG. 12 is an elevated perspective view of the U-shaped section of the hinged-open head and the snap mounted floss tip.

The interior space 95 formed in the apex 90 upon closure of the top and bottom sections 91,93 is used to house the anterior portion 105 of the output shaft 100, the floss tip 120 and the contact sensor mechanism 110.

Figure 14:
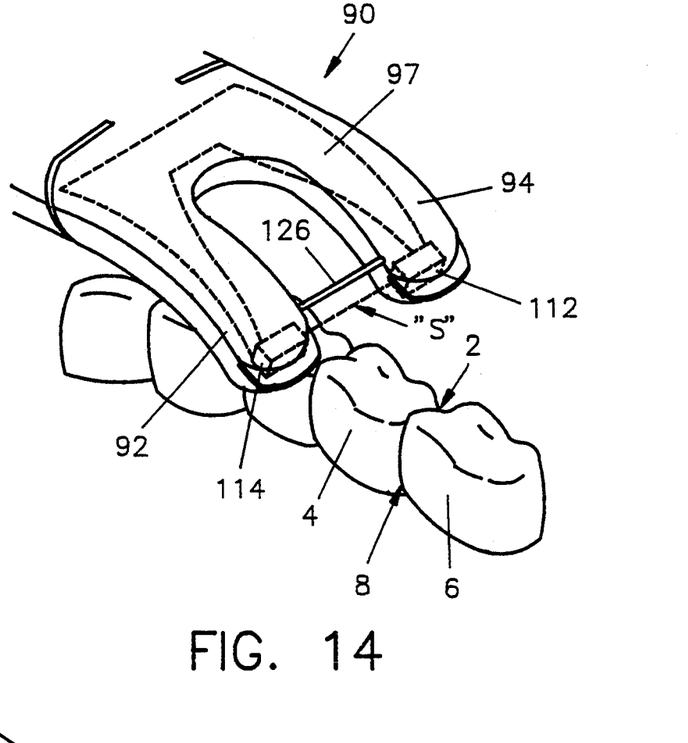
FIG. 14 is an elevated environmental view of the U-shaped end of the head shown above teeth with, in hidden view a contact sensor mechanism in the prongs.
Figure 15:
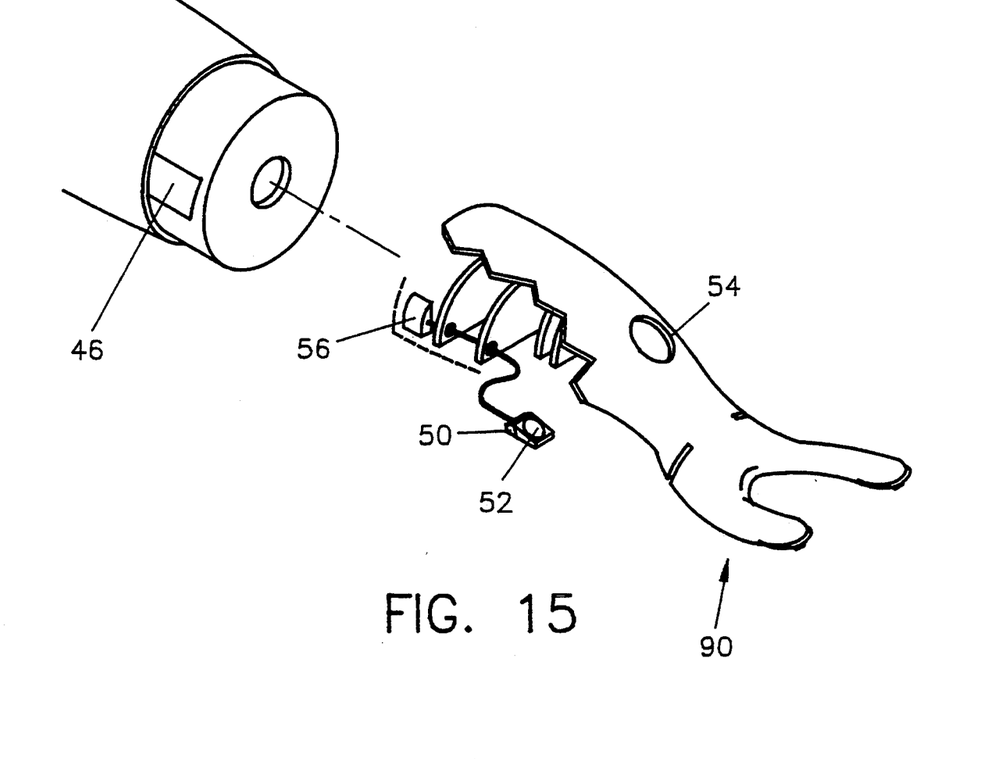
FIG. 15 is an elevated view of a partially cut away section of the head showing the contact connections for the light to the motor housing unit.

As best shown in FIG. 14, the contact sensor mechanism 110 is preferably a pair of infrared sensors 112, 114 embedded or mounted in the ends of the plastic fingers 92,94. Any disruption of the line of sight "S" between the prongs 92,94 is detected by the sensors 112,114. As can be seen in FIG. 114, the line "S" will be broken just prior to contact between the floss filament 126 and a contact area 2 between the two teeth 4 and 6. The disruption of the line "S" is signalled to a mylar printed circuit board 96 which is wired (not shown) to the second electrical contact 46 on the collar 40. A signal is sent to the switch 39 to activate the motor 34.

Figure 16:
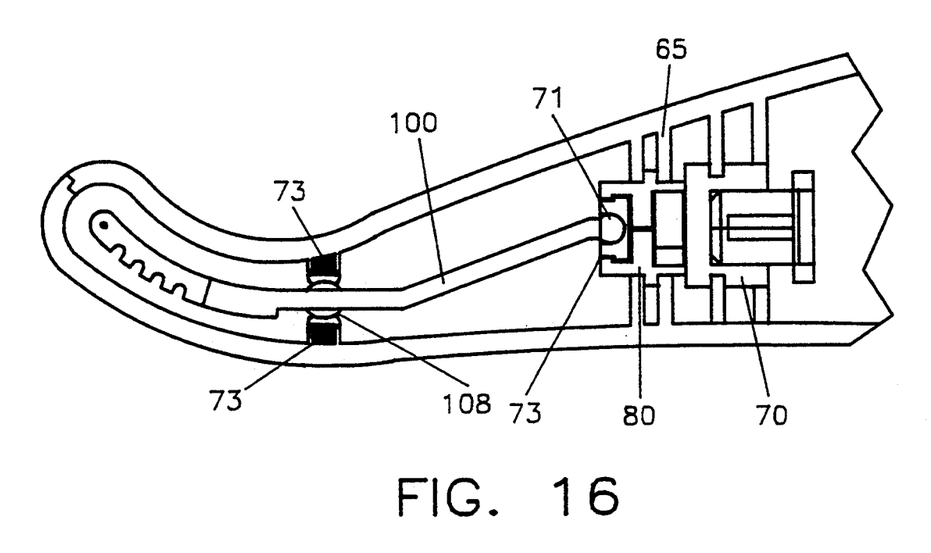
FIG. 16 is a side sectional view of the shaft cushioned by springs positioned at the pivot mount location and showing a mechanical clutch device and slip gear for engaging, or disengaging, the shaft.

It will be recognized by those skilled in the art that the contact sensor mechanism 110 may be other electronic sensing devices such as fiber optics systems, a micro-switch, or a stress sensor attached to the shaft 100. Pressure on the floss filament 126 would cause a change in resistance to activate the motor 34. Alternatively, a conventional mechanical clutch device with a slip gear could be used in place of the electronic sensors as shown in FIG. 16. In this method, the shaft 100 is supported on its top and bottom surfaces by springs 73 which cause the shaft to free wheel in the absence of tension applied to the floss filament 126. When pressure is applied to the filament 126, the shaft is displaced into the moving yoke 80 to commence the Z-shaped pattern of motion.

THE FLOSS TIP 120

Figure 13A:
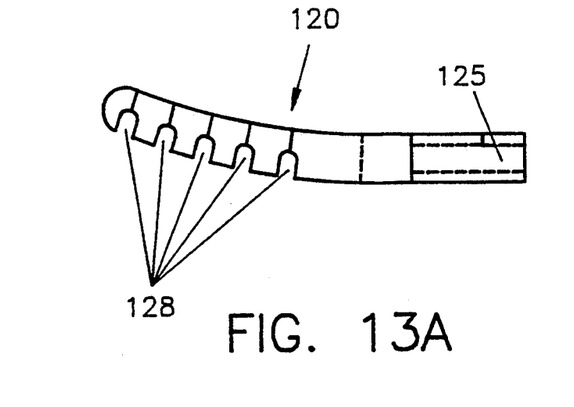
FIG. 13A is a side view of the floss tip.
Figure 13B:
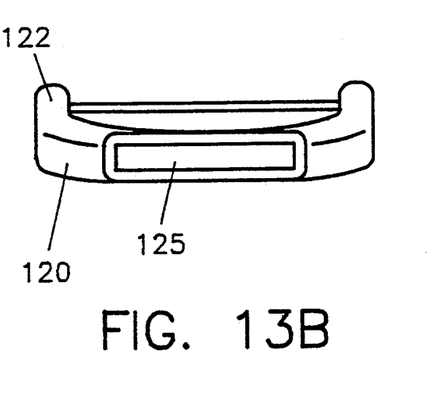
FIG. 13B is a rear plan view of the floss tip.

The disposable floss tip 120 is injection molded from a food grade resilient plastic, preferably polyethylene. The U-shaped tip 120 defines a pair of tines 122, 124 with a floss filament 126 spanning the tines and molded into the U-shaped tip 120 during fabrication. The floss filament is preferably made from ultra-high molecular weight polyethylene (UHMWPE) having a tensile strength of approximately $375-435 \times 10^3$ psi, a tensile modulus of elasticity of $17-25 \times 10^6$ psi, elongation factor of 2.7–3.5 percent, specific strength index of $10.7-12.4 \times 10^6$, and a specific modulus index of $486-714 \times 10^6$. The floss filament may be made from conventional dental floss, although some shredding of conventional nylon floss may occur. A plurality of spaced notches 128 are formed in the two tines 122,124 of the floss tip 120. A mating generally rectangular, snap-in interface 125 enables the floss tip 120 to attach over the mounting fingers 107 of the output shaft 100. A release tab 127 depresses snap-release 109.

As can best be seen in FIG. 3, the output shaft 100 supports the floss tip 120 centrally and transfers the Z-shaped pattern of motion to the tip 120. The tines 122,124 extend laterally from the output shaft 100 and are free to bend and flex vertically within the interior 95 of the apex 90 in response to stress applied to the floss filament 126. With the exception of the floss filament 126, the entire floss tip 120 is inside of the apex 90 during flossing operations. The notches 128 and the U-shape of the floss tip 120, in conjunction with the shock-absorbing properties of the resilient plastic, enable the floss tip 120 to absorb the 2 mm vertical motion component of the Z-shaped movement of the output shaft 100 under certain operating conditions to be described below. The number of the notches 128 may be varied and the shape may be other than U-shaped for aesthetic purposes.

CLEANING MOTION OF FLOSSER 10

As described above, the user may operate the flosser 10 in manual or automatic modes. Referring to FIG. 14 and operating in the automatic mode, the user preferably orients the flosser 10 with the curved apex 90 of the head 60 extending below the axis "A" of the flosser for flossing the bottom teeth. The flosser 10 is inverted to extend the apex above the axis "A" to floss the top teeth. The curved apex 90 is the only portion of the flosser 10 to approach the teeth.

As the floss filament 126 approaches the contact point 2 between the teeth 4,6, the infra-red sensors 112 cause the circuit board 96 to signal the switch 39 to activate the motor 34. The rotational motion of the motor shaft 35 is transmitted to the engaged motor linkage 37 which in turn causes the attached cam 70 to rotate. As the cam 70 rotates, the offset peg 76 of the cam 70 is rotated in an eccentric pattern of motion within the slot 84 of the yoke 80 because of the 3 mm offset position of the peg 76. The eccentric motion of the peg 76 within the slot 84 is translated to 3 mm of horizontal motion of the yoke 80, 1.5 mm to the right and 1.5 mm to the left, as the peg 76 pushes against the sides of the walls of the slot 84 causing the yoke 80 to slide within the seating slot 68. The 2 mm of vertical motion is supplied to the shaft 100 as the cam follower 106 follows the vertical component of the Z-shaped tracking surface 69.

When pressure is applied to the floss filament 126 through contact entering and exiting the contact point 2, the floss tip 120 with stress relieving notches 128 on each tine absorbs the 2 mm vertical component of the Z-shaped pattern of motion thereby producing only horizontal movement of the floss filament 126 at the tight contact areas of the teeth. When the floss filament 126 passes through the contact point into the interproximal area 8 between the two teeth, the pressure on the filament is relieved thereby enabling the Z-shaped pattern of motion to be resumed. The absorption of the vertical component prevents chatter of the floss on the teeth, deflection of the device from the teeth, and injury to the gingiva when the floss filament passes easily and safely through the tight contact point. The floss filament 126 is then free to move primarily up and down in the Z-shaped pattern of motion against the interdental surfaces of the two teeth.

In another aspect of the present invention, the floss tip 120 is detachable for cleaning purposes and includes conventional channel or eyelet mounts for attaching removable dental floss filament. Alternatively, the floss filament may be constructed in set lengths with loops at each end to fit over the tines of the tip 120.

To those skilled in the art to which the present invention pertains, many widely varying embodiments and implementations of the principles of the present invention will be suggested from the foregoing. For instance, the case gasket may be replaced by collar mounts as shown in the head and motor casing mounting method, and the battery and motor section may be sealed to form a unitary section. The grooves 128 may be changed o other configurations and other spacing patterns, and may be further modified for aesthetic purposes. The motor may be a conventional step-down motor. A potentiometer may be provided to reduce the RPM's of the motor. The internal components of the flosser ay be molded from other suitable substances such as nylon or Delrin (tm). The Z-shaped pattern of motion may be provided with other camming arrangements, the 3/2 mm horizontal/vertical movement may vary slightly, and the RPM's may vary. The description and the disclosures presented herein are by way of illustration only and should not be considered to limit the present invention, the scope of which is more particularly set forth in the following claims.

What is claimed is:

1. A powered dental flossing device comprising:
   a housing;
   a power source;
   motion translation means operatively connected to the power source for producing a bidirectional pattern of motion having horizontal and vertical components relative to a vertical side surface of the teeth;
   cleaning tip means operatively connected to the motion translation means and having filament means that outputs the bidirectional pattern of motion; and
   means for producing only the horizontal component at the filament means in a first phase in response to pressure above a predetermined amount on the filament at a contact area between two teeth and for providing both the horizontal and vertical component at the filament means in a second flossing phase in an interproximal area between said two teeth.

2. The flossing device of claim 1 further comprising at least one head means attached to the housing means and housing the motion translation means.

3. The flossing device of claim 2 wherein the cleaning tip means is disposable.

4. The flossing device of claim 3 wherein the head means defines means for exposing the cleaning tip means for removal therefrom.

5. The flossing device of claim 2 further comprising sensing means for detecting the filament means in proximity to the teeth.

6. The flossing device of claim 5 further comprising a switch means operatively connected to the sensing means for signalling activation of the power source.

7. The flossing device of claim 6 wherein the sensing means comprises infrared sensors for detecting the filament means in proximity to the teeth.

8. The flossing device of claim 6 wherein the sensing means comprises stress sensor means for detecting contact between the filament means and the teeth.

9. The flossing device of claim 6 wherein the sensing means comprises electric switch means for detecting contact between the filament means and the teeth.

10. The flossing device of claim 6 further comprising illumination means operatively connected to the switch means for illuminating the teeth.

11. The flossing device of claim 2 wherein the means for producing only the horizontal component is a shock-absorbing material for absorbing the vertical component while the filament means is in a contact area between two teeth.

12. The flossing device of claim 11 wherein the cleaning tip means is made from the shock-absorbing material.

13. The flossing device of claim 11 wherein a shaft of the motion translating means is made from the shock-absorbing material.

14. The flossing device of claim 2 wherein the means for producing only the horizontal component is a mechanical clutch for disengaging production of the vertical component by the motion translation means while the filament means is in a contact area between two teeth.

15. The flossing device of claim 2 wherein the means for producing only the horizontal component is at least one spring means for dampening the vertical component while the filament means is in a contact area between two teeth.

16. The flossing device of claim 2 wherein the means for producing only the horizontal component is a sensor for deactivating the vertical component while the filament means is in a contact area between two teeth.

17. The flossing device of claim 1 wherein the power source comprises a motor energized by a battery having a recharging means.

18. The flossing device of claim 17 wherein the motor operates at an RPM and a torque sufficient to overcome a contact friction of the teeth.

19. The flossing device of claim 2 wherein the motion translation means comprises a cam means connected to a yoke means, the yoke means further connected to an output shaft, the output shaft having cam follower means for following a tracking surface.

20. The flossing device of claim 19 wherein the cam means provides the horizontal component of the bidirectional pattern of motion, and the tracking surface provides the vertical component.

21. The flossing device of claim 2 wherein the at least one head means comprises a plurality of interchangeable, individualized, removable heads.

22. A powered dental flossing device comprising:
a housing means;
a power source within the housing means;
motion translation means attached to the power source for outputting a bidirectional pattern of motion having a vertical component relative to a vertical side surface of the teeth and a horizontal component;
at least one removable head means housing the motion translation means;
tip means attached to the motion translation means and having filament means outputting the bidirectional pattern of motion; and
means for dampening the vertical component in response to pressure above a predetermined amount on the filament means in a contact area between two teeth.

23. The flossing device of claim 22 wherein the tip means is disposable.

24. The flossing device of claim 22 further comprising sensing means for detecting the filament means in proximity to the teeth.

25. The flossing device of claim 24 further comprising a switch means operatively connected to the sensing means for signalling the battery to activate the power source.

26. The flossing device of claim 24 wherein the sensing means comprises infrared sensors for detecting the filament means in proximity to the teeth.

27. The flossing device of claim 24 wherein the sensing means comprises stress sensor means for detecting contact between the filament means and the teeth.

28. The flossing device of claim 24 wherein the sensing means comprises electric switch means for detecting contact between the filament means and the teeth.

29. The flossing device of claim 24 further comprising light means operatively connected to the switch means for illuminating the teeth.

30. The flossing device of claim 22 wherein the power source comprises a motor energized by a battery.

31. The flossing device of claim 22 wherein the motion translation means comprises a cam means defining first attachment means for connection at a first end to the power source and second attachment means at a second end for connection to a yoke means, the yoke means further connected to an output shaft, the output shaft having cam follower means for following a tracking surface.

32. The flossing device of claim 31 wherein the cam means provides a horizontal component of the bidirectional movement, and the tracking surface includes a vertical track section for providing the vertical component of the bidirectional movement.

33. A dental flossing unit for operative engagement by a low powered device having an output shaft, the flossing unit comprising:
a housing;
motion translation means in the housing and operatively connected to the output shaft for outputting a bidirectional pattern of motion having horizontal and vertical components;
cleaning tip means operatively connected to the motion translation means and defining filament means; and
means for producing only the horizontal component in response to pressure above a predetermined amount on the filament means encountered at a contact area between two teeth and for producing both the horizontal and vertical components while the filament means is in an interproximal area between said two teeth.

34. The flossing device of claim 33 further comprising sensing means for detecting the filament means in proximity to the teeth.

35. The flossing device of claim 34 further comprising a switch means operatively connected to the sensing means for signalling activation of the powered device.

36. The flossing device of claim 34 wherein the sensing means comprises infrared sensors for detecting the filament means in proximity to the teeth.

37. The flossing device of claim 34 wherein the sensing means comprises stress sensor means for detecting contact between the filament means and the teeth.

38. The flossing device of claim 34 wherein the sensing means comprises electric switch means for detecting contact between the filament means and the teeth.

39. The flossing device of claim 34 further comprising light means operatively connected to the switch means for illuminating the teeth.

40. The flossing device of claim 33 wherein the motion translation means comprises a cam means defining first attachment means for connection at a first end to the shaft of the powered device and second attachment means at a second end for connection to a yoke means, the yoke means further connected to an output shaft, the output shaft having cam follower means for following a tracking surface.

41. The flossing device of claim 40 wherein the cam means provides the horizontal component of the bidirectional movement, and the tracking surface includes a vertical track section for providing the vertical component of the bidirectional movement.

42. The flossing device of claim 33 wherein the means for producing only the horizontal component is a shock-absorbing material for absorbing the vertical component when the filament means is in a contact area between two teeth.

43. The flossing device of claim 42 wherein the cleaning tip means is made from the shock-absorbing material.

44. The flossing device of claim 42 wherein a shaft of the motion translating means is made from the shock-absorbing material.

45. The flossing device of claim 33 wherein the means for producing only the horizontal component is a mechanical clutch for disengaging production of the vertical component by the motion translation means while the filament means is in a contact area between two teeth.

46. The flossing device of claim 33 wherein the means for producing only the horizontal component is at least one spring means for dampening the vertical component while the filament means is in a contact area between two teeth.

47. The flossing device of claim 33 wherein the means for producing only the horizontal component is a sensor for deactivating the vertical component while the filament means is in a contact area between two teeth.

48. The flossing device of claim 33 wherein the powered device operates at an RPM and a torque sufficient to overcome a high contact friction produced by substantial contact between tow teeth.

49. The flossing device of claim 33 wherein the head means defines means for exposing the cleaning tip means for removal therefrom.

50. A floss tip made from a resilient plastic material, the floss tip for attachment to a dental flossing device having a tip mounting means, the floss tip comprising:
a unitary body having a first end and a second end;
an attachment means defined in the first end for attaching the floss tip to the tip mounting means;
a pair of tines defined in the second end, each tine having at least one notch defined therein; and
a floss filament means spanning the pair of tines, the at least one notch in conjunction with the resilient plastic material absorbs a vertical powered motion component of the dental flossing device when sufficient pressure is applied to the floss filament means.

51. The floss tip of claim 50 wherein the tip is removable and disposable.

* * * * *